United States Patent [19]

Kincade et al.

[11] Patent Number: 5,494,899
[45] Date of Patent: Feb. 27, 1996

[54] SELECTIVE REGULATION OF B LYMPHOCYTE PRECURSORS BY HORMONES

[75] Inventors: Paul W. Kincade, Oklahoma City; Kay Medina, Moore, both of Okla.

[73] Assignee: Oklahoma Medical Research Foundation, Oklahoma City, Okla.

[21] Appl. No.: 224,236

[22] Filed: Apr. 7, 1994

Related U.S. Application Data

[63] Continuation-in-part of Ser. No. 44,280, Apr. 7, 1993, abandoned.
[51] Int. Cl.$^6$ ............... C07K 14/575; C07K 14/59; A61K 31/56; A61K 38/24
[52] U.S. Cl. ............... 514/21; 514/177; 514/182; 514/841; 514/843; 530/399; 530/850; 530/851; 530/852; 530/853; 530/854
[58] Field of Search .................. 514/21, 841, 843, 514/177, 182; 530/399, 850, 851, 852, 853, 854

[56] References Cited

U.S. PATENT DOCUMENTS

| | | | |
|---|---|---|---|
| 4,383,993 | 5/1983 | Hussain et al. | 514/177 |
| 4,885,290 | 12/1989 | Asano et al. | 514/182 |
| 4,894,373 | 1/1990 | Young | 514/239.2 |
| 4,900,734 | 2/1990 | Maxson et al. | 514/171 |

OTHER PUBLICATIONS

Kotani, et al. "Effects of Estrogen on the Lymphac Regeneration & Immune Response In Irradiated & Marrow Reconstituted Mice" Acta Anat. 105 298–308 1979.

Nikolaevich, et al. "Major Reproduction Hormones as Regulators of Cell to Cell Interactions In Humoral Immune Responses" Brain, Behav., Immun. 5 149–161 1991.

Chakraborty et al. "Effects of Long–Term Treatment w/Estradiol or Clomiphene Citate On Bone Maintenance and Pituitery & uterine weights In Ovariectomyed Rats" J Steroid Biochem Molec. Biol. 40(4–6) 725–729 1991.

Gray et al. "Hormones In Blood" pp. 148–149 1983.

VanVoorhis et al. "The Effects of RU 486 on Immune Function & Steroid–Induced Immunosuppression In Vitro" J. Clin. Endonin Metab. 69(6) 1195–1191 1989.

Greenstein et al. "Aromatase Inhibitors Regenerate The Thymus In Aging Male Rats" Int J Immunopharmacol. 14 (4) 541–553 1992.

Beamer, W. G., et al., "Granulosa Cell Tumorigenesis in Genetically Hypogonadal–immunodeficient Mice Grafted with Ovaries from Tumor-susceptible Donors," Cancer Res. 53:3741–3746 (Aug. 15, 1933).

Engelhard, D., et al., "Cycling of Peripheral Blood and Marrow Lymphocytes in Cyclic Neutropenia," Proc. Natl. Acad. Sci. 80:5734–5738 (Sep. 1983).

*Primary Examiner*—Michael G. Wityshyn
*Assistant Examiner*—Nancy J. Degen
*Attorney, Agent, or Firm*—Arnall Golden & Gregory

[57] ABSTRACT

It has been determined that estrogen and other hormones elevated in pregnancy induce a specific modulation of lymphocyte precursor cell production. The immune system of an animal or bone marrow cells in culture can therefore be modulated in a specific manner by administration of hormones elevated during pregnancy, such as estrogen and estrogen-like compounds or compounds that interfere with the synthesis or activity of these hormones, to increase or decrease production of B lymphocyte precursor cells.

13 Claims, 5 Drawing Sheets

SELECTIVE REGULATION OF B LYMPHOCYTE PRECURSORS BY HORMONES

This is a continuation-in-part of U.S. Ser. No. 08/044,280 entitled "Selective Regulation of B Lymphocyte Precursors by Hormones" filed Apr. 7, 1993, by Paul W. Kincade and Kay Medina, now abandoned.

BACKGROUND OF THE INVENTION

The present invention is generally in the area of immunoregulation, and is particularly the selective hormone-mediated modulation of lymphocyte production in bone marrow.

The production of lymphocytes and other blood cells is a carefully regulated process that is essential for maintenance of a normal immune system. B lymphocytes, which upon activation differentiate into plasma cells that secret antibodies, originate in bone marrow from stem cell precursors. Another major category of lymphocytes, T lymphocytes, is made in the thymus from stem cell precursors. Together these lymphocytes are responsible for both the humoral (antibody) mediated immune response and the cell mediated immune response.

Studies of molecular regulators of B lymphopoiesis have focused on aspects that might be organ, i.e., bone marrow, specific, though no regulatory molecules have been found that are unique in distribution to that tissue. Blood cell formation within bone marrow is thought to be controlled in part by close cellular interactions and the availability of cytokines that induce proliferation and differentiation of committed precursor cells. However, understanding of the proliferative, developmental, and differentiative aspects of this process is incomplete, especially of mechanisms that inhibit or increase the production of particular blood cell types.

There is a gradual involution of the thymus with age, but the mechanism through which this occurs is only partially understood. It has long been known that the thymus involutes further during pregnancy and regrows after delivery. This phenomenon is believed to be regulated in part by hormones, because estrogen injections have been observed to cause thymus atrophy similar to that associated with pregnancy. However, the immune system is thought to function normally during pregnancy; that is, the host defense against pathogens appears to be intact.

A better understanding of the influence of hormones on the humoral immune system is needed. This information may be relevant to maternal-fetal relationships during pregnancy and abnormalities involving them, and to the pathophysiologic mechanisms of autoimmune diseases such as systemic lupus erythematosus (SLE), which are commonly diagnosed or may worsen during pregnancy. Information on the effects of hormones on the humoral immune system may also be relevant in cyclic neutropenia and diseases in which antibodies are directed against cell components. An increased awareness of the effects of hormone administration may also be helpful in treating immune deficiency diseases, especially those in which the numbers of lymphocytes are abnormal, and in preventing iatrogenic disease or the side effects of hormone replacement therapy, as in the use of hormones in the treatment of osteoporosis. It may also be possible to use this basic information to manipulate immunologic tolerance and achieve immunosuppression, or alternatively, with agents that interfere with the synthesis or activity of hormones, to augment the humoral immune system. Moreover, methods for propagating lympho-hemopoietic progenitor cells and stem cells in culture might be improved by manipulation of hormone concentrations in cell culture medium.

It is therefore an object of the present invention to provide a method for immunomodulation through manipulation of specific classes of immune cells, especially B lymphocytes, by administration of compounds having an effect on the number of B lymphocyte precursors and on the resulting number of newly formed B lymphocytes and plasma cells.

It is a further object of the present invention to provide methods and means for manipulation of B lymphocytes and their precursor cells and plasma cells involved in autoimmune disorders, osteoporosis, and cyclic neutropenia.

It is another object of the present invention to provide methods and means for manipulation of B lymphocytes and their precursor cells and plasma cells involved in immune deficiency diseases.

It is yet another object of the present invention to provide methods and means to improve cell culture of the cells of bone marrow and its stroma.

SUMMARY OF THE INVENTION

Based on the discovery that normal pregnant mice have a striking reduction in the number of committed precursors of B lymphocytes in bone marrow, which could be documented in mice as early as day six of gestation, when the number of IL-7 responding colony forming cells was reduced by as much as two-thirds of normal levels, it was determined that estrogen and other hormones that are elevated in pregnancy induce a specific down-regulation of B lymphocyte precursor cell production by proliferation or differentiation during pregnancy and lactation. This down-regulation was also induced by administration of specific hormones in animals that were not pregnant or lactating. Similar effects were observed with administration of progesterone, but only in combination with estrogen.

It was also discovered that the number of IL-7 responsive B lymphocyte precursors was greatly expanded in genetically hypogonadal female mice that have a secondary deficiency in gonadotropin synthesis and gonadal steroidogenesis. This demonstrates that the reduction in the level or function of endogenous sex steroid hormones, gonadotropins, or gonadotropin releasing hormones (GNRH) can cause an increase in the number of B lymphocyte precursor cells and ultimately a resulting expansion in the production of B lymphocytes.

These discoveries allow modulation of the immune system of an animal in a specific manner by administration of hormones that are elevated during pregnancy, such as estrogens, estrogen-like compounds, and related steroids; synthetic analogues of these hormones; eliciting agents of the hormones, such as gonadotropin releasing hormones and gonadotropins; or agents that interfere with the synthesis or activity of these hormones, such as agonists, antagonists, competitive inhibitors, inactivators, or blockers, alone or in combination.

The ability to modulate the production of B lymphocyte precursor cells by proliferation or differentiation and thereby the immune system by administration of hormones can be used to enhance immune tolerance during pregnancy and to treat a number of disorders, especially those found in very high percentages of women as compared with men, such as many of the autoimmune disorders; cyclic neutropenia;

osteoporosis; and immune deficiency diseases. There are also applications in the culture of mammalian cells, since many of the culture media include a dye such as phenol red as a pH indicator, which has estrogen-like properties, and/or include animal serum with nonphysiologic hormone concentrations that may not be beneficial for culture of lymphocyte precursors and other cells that have similar requirements.

BRIEF DESCRIPTION OF THE DRAWINGS

FIG. 2A represents B lineage cells in normal control mice. FIG. 2B shows B lineage cells at 17 days gestation. FIG. 2C represents B lineage cells at 18 days gestation. FIG. 2D shows B lineage cells at term.

DETAILED DESCRIPTION OF THE INVENTION

Figure 1:
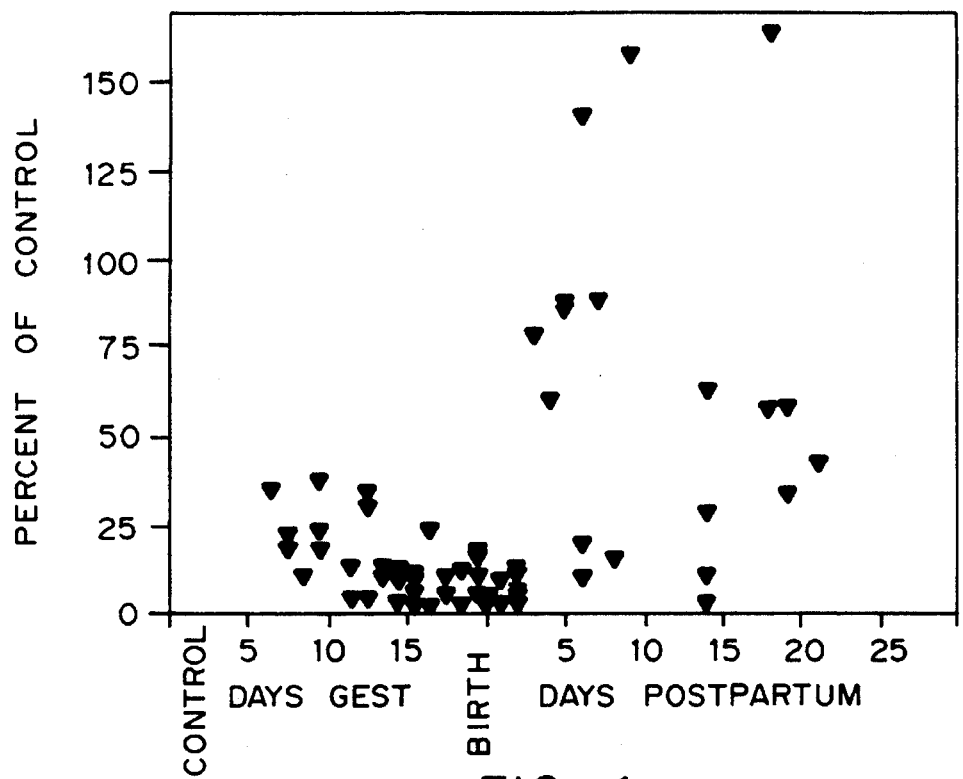
FIG. 1 is a graph showing numbers of IL-7 responsive B lineage precursors versus days of gestation and days postpartum for normal mice, expressed as the percent of control. Bone marrow cells were obtained from BALB/c mice at various stages of pregnancy and during the postpartum period and placed in semisolid agar with interleukin 7. The numbers of proliferating foci were determined after six days of culture.

Nomenclature.

As used herein, the nomenclature representing the stages of differentiation and development of B lymphocytes and their committed precursor cells from early to mature is as follows: Very early B lymphocyte precursors are TdT$^+$, CD45R$^+$, HSA$^{lo}$, CD43$^+$, and are also called "fraction A" cells. Pro-B and large pre-B lymphocyte precursors are CD45R$^+$, HSA$^{hi}$, CD43$^+$, are also called "fraction C" cells, and are the interleukin-7 (CFU-IL7) responsive cells. Small pre-B lymphocyte precursors are CD45R$^+$, HSA$^{hi}$, CD43$^-$, are also called "fraction D" cells, synthesize the mu chain of IgM but do not display sIgM (IgM$^-$ or $\mu^-$), and do not synthesize or display IgD (IgD$^-$ or delta$^-$). Immature B lymphocytes synthesize and display IgM but not IgD ($\mu^+$, delta$^-$ or IgM$^+$, IgD$^-$). Mature B lymphocytes display both IgM and IgD as surface markers ($\mu^+$ or IgM$^+$ and delta$^+$ or IgD+). All B lineage cells, including mature B lymphocytes, are unique in their display of the CD45R surface marker, while earlier stages of B lymphocyte precursor cells also display the CD43 surface marker, which is lost after the large pre-B stage in the B cell developmental process.

Other parenchymal cells in bone marrow include the erythroid cell lineage, characterized by the TER surface marker; macrophages and neutrophils, identified as Mac-1 cells; and macrophage and granulocyte progenitor cells, identified as CFU-c cells.

Modulation of B lymphocyte precursor cell numbers by administration of hormones.

In vivo modulation.

Mice are considered to be a predictive model for hormone control in humans. Based on studies in mice, it has been discovered that during pregnancy, when the endogenous levels of hormones associated with pregnancy are elevated, a drastic and selective decline in the number of B lymphocyte precursor cells, including IL-7 responsive cells, large and small pre-B cells, and immature B lymphocytes, occurs in murine bone marrow, without corresponding changes in myeloid and erythroid cells. The same changes were induced by administration of sex steroid hormones to normal, non-pregnant female animals.

It was also discovered that, using a mouse model for decreased levels of sex hormones, mice that are genetically deficient in gonadotropin releasing hormones, gonadotropins, and sex steroid hormones, as well as castrated male mice that lack significant levels of androgens that can be converted to estrogens, a marked increase in the total number and same subpopulations of B lymphocyte precursor cells in bone marrow can be induced, without a corresponding increase in erythroid or myeloid cells. Administration of a sex hormone in the genetically deficient animals significantly reduced the numbers of B lymphocyte precursors.

Based on these discoveries, methods have been developed using hormones to modulate the production of mammalian bone marrow B lymphocyte precursor cells by proliferation or differentiation in vivo by exposing the cells to the hormones.

Hormones that are useful to influence B lymphopoiesis.

Hormones that decrease the production of B lymphocyte precursor cells.

Hormones that can be used are those that are elevated during pregnancy and their synthetic analogues, eliciting agents of the hormones elevated during pregnancy, and agents that interfere with the synthesis or activity of the hormones elevated during pregnancy.

Examples of hormones that are elevated during pregnancy and useful to negatively modulate B lymphopoiesis include estrogen, estrone, estradiol, estriol, progesterone, human chorionic gonadotropin (HCG), human placental lactogen, prolactin, and cortisol, and the synthetic analogues of these hormones, alone or in combination. Further, the production of B lymphocyte precursor cells by proliferation or differentiation can also be decreased by hormone eliciting agents, preferably gonadotropin releasing hormones ("GNRH") such as luteinizing hormone, and gonadotropins such as follicle stimulating hormone and luteinizing hormone, which are also elevated during pregnancy. GNRHs stimulate production of gonadotropins, elevating their levels during pregnancy and at other times in the menstrual cycle, and these in turn mediate the production of the sex steroids and other hormones elevated in pregnancy. All of these are available commercially from Sigma Chemical Co. (St. Louis, Mo.) and a variety of other pharmaceutical suppliers.

Hormones that increase the production of B lymphocyte precursor cells.

The production of B lymphocyte precursor cells can be positively modulated with agents that interfere, directly or indirectly, with the synthesis or activity of hormones that are elevated during pregnancy or their eliciting agents. Examples of such agents include agonists, antagonists, competitive inhibitors, inactivators, and blockers of the hormones that are elevated during pregnancy. These agents can act at the level of the sex steroid hormones, gonadotropins, or gonadotropin releasing hormones, or upon the cells that produce these hormones, to achieve the direct or indirect interference in synthesis or activity.

Examples of agents that can interfere with the synthesis or activity of hormones elevated during pregnancy include agents that inhibit progesterone action, such as RU 486 (from Roussel-UCLAF, Romainville, France); block estrogen responses, such as ICI 182,780 (Zeneca Pharmaceuticals, U.K.); block the conversion of androgen to estrogen, such as aromatase inhibitors, as, for example, 1,4,6-androstatriene-3,17-dione and 4-hydroxyandrostenedione (Ciba-Geigy Pharmaceuticals, West Sussex, U.K.); and block the pituitary and prevent the release of FSH and LH, such as GNRH agonists, as, for example, ICI 118630 (also known as Zoladex, an LHRH analogue, from ICI, Macclesfield, Cheshire, England). Tamoxifen, another compound that may be useful, has both estrogen and anti-estrogen activities, as does RU 486, but is species specific in some respects.

Therapeutic Applications.

Administration of an Effective Dosage

In a preferred embodiment for in vivo modulation, a quantity of the hormone effective in inducing the desired modulation in the production of B lymphocyte precursors by proliferation or differentiation is administered to a mammal, preferably a human. The preferred method of administration is by implantation of a controlled release device containing the hormone, although the hormone can also be administered by other modes, for example orally, by injection, or by dermal patch. The administration of the hormone can be adjusted in frequency and duration to achieve the desired increase or decrease in the production of B lymphocyte precursor cells, as determined by the routine assays described below and in the examples.

The hormones are used alone or in combination in an amount effective to produce the desired modulation in B lymphocyte precursor cell production, as readily determined in vitro by techniques known in the art and described in the examples, for example, colony assays and flow cytometry of bone marrow and/or precursor cell samples. A preferred amount of estrogen or other hormones elevated during pregnancy is an amount sufficient to simulate the range of endogenous serum concentrations found during pregnancy, and is more preferably a starting amount to achieve a concentration of less than 100 ng/ml of hormone in serum, which can be adjusted to achieve the desired results. A preferred starting amount of an agent that interferes with the synthesis or activity of the hormones elevated during pregnancy is less than 1 mg/kg body weight, which can also be adjusted to achieve the desired results.

Autoimmune Disorders.

The specific action of hormones in autoimmune disorders has not been elucidated. However, there are indications that hormones affect the function of mature antibody forming B cells and plasma cells and that hormones may participate in diseases involving these cells. For example, the disease systemic lupus erythematosus (SLE) is ten times more prevalent in women, and is often first diagnosed or exacerbated during pregnancy. The sex preference for susceptibility to lupus in female autoimmune mice and humans can be reversed by castration or hormone administration.

Experiments with autoimmune prone mice, New Zealand Black (NZB), implicate sex hormones in autoimmune diseases. Previous studies showed that B lymphocyte precursors in this strain of animals appear at an elevated rate during embryonic life compared to normal, and decline at an accelerated rate during postnatal life. This may reflect an abnormal production of or responsiveness to hormones, as reported by Jyonouchi et al., *J. Exp. Med.* 159:1277 (1984) and Jyonouchi et al., *J. Exp. Med.* 155:1665 (1982). Studies indicate that there is endocrine participation in autoimmune manifestations in this model.

Accordingly, it is believed that hormones, including the hormones that are elevated during pregnancy and their synthetic analogues and eliciting agents, and agents that interfere with the synthesis or activity of these hormones, or combinations thereof can be administered selectively to patients, particularly women, who have autoimmune disorders to immunomodulate production of B lymphocyte precursor cells and thereby immunomodulate these disorders. This presents a very favorable alternative to the steroid therapy now in use.

Treatment of Immune Deficiency Diseases.

Immunodeficiency syndromes may be congenital, spontaneously acquired, or iatrogenic. Patients are characterized by marked susceptibility to infection, autoimmune disease, and sometimes lymphoreticular malignancies. Recurrent or chronic sinopulmonary infection, meningitis, and bacteremia are hallmarks of patients with defects in humoral immunity. Humoral immunodeficiency also plays a role in susceptibility to viral infection, such as chickenpox and measles, hepatitis, poliomyelitis, encephalitis, and influenza, and in susceptibility to parasitic infestations. Humoral immunodeficiency may be associated with lymphocytopenia, antibody deficiency, or both.

It is believed that administration of agents that interfere with the synthesis or activity of the hormones that are elevated during pregnancy, particularly when the result is a lowering of the levels of sex steroid hormones, can increase production of B lymphocyte precursor cells and ultimately mature B cells and plasma cells in patients with immune deficiency syndromes, especially those associated with lymphocytopenia. Agents that are believed to be useful in this context include agonists, antagonists, competitive inhibitors, inactivators, and blockers of the pregnancy-related hormones.

An example of an immune deficiency disease that may respond to treatment with hormones is cyclic neutropenia. Studies conducted with patients, as described by Engelhard et al., *Proc. Natl. Acad. Sci.* 80:5734 (1983), indicate that boys with cyclic neutropenia have a deficiency of neutrophilic granulocytes at regular intervals. It has been found that numbers of pre-B cells in bone marrow increase precisely when numbers of myeloid cells decline. This abnormality may be related to hormonal dysfunction and may respond to hormones that suppress the production of B lymphocyte precursors at certain stages.

Thus, diagnostic procedures for immune deficiencies and autoimmune diseases in both men and women, leukemias, and other disorders should be greatly improved with knowledge of the effects of hormones on the humoral immune system.

Treatment of Bone Marrow Transplants.

Steroid hormones may be important regulators of normal lymphopoiesis. Senescence of the immune system could in part be related to hormonal influences on lymphocyte precursor numbers. As a result, knowledge of the influence of hormones on lymphopoiesis is useful for designing conditions favorable for long term cultures. It is also useful in designing treatments of bone marrow harvested for transplantation, both before and after transplantation. For example, hormones are believed to modulate expression and/or function of cell adhesion molecules in bone marrow, which would result in mobilization of stem cells or committed precursors into the blood stream. These could then be conveniently collected and used for bone marrow transplantation. Treatment of bone marrow donors with certain hormones before transplantation to deplete potential recipient reactive lymphocytes or to modify the homing behavior of stem cells in recipients should also be useful.

Iatrogenic Effects of Hormone Therapy.

Estrogens are currently used to prevent osteoporosis. Compounds such as tamoxifen, which has estrogen-like activity, are employed for breast cancer therapy. A better understanding of the effects of such agents on precursor cells in bone marrow is relevant to identifying potential side effects and developing strategies for modifying the same.

Applications in cell culture.

In vitro modulation.

Long term bone marrow culture (LTBMC) studies were performed to identify potential cellular targets of estrogen action and evaluate other effective hormones. Appropriate doses of estrogen and progesterone selectively inhibited production of lymphoid, but not myeloid, cells by proliferation or differentiation in LTBMC. Addition of human chorionic gonadotropin (HCG) stimulated growth of the adherent layers in such cultures.

Hormones that were tried in this context include 17 β-estradiol (E2), progesterone, dehydroepiandrosterone (DHEA), DHEA sulphate, prolactin, and growth hormone. The hormones had no significant influence on growth of established myeloid cell lines, clonable pre-B cells, or an IL-7 dependent pre-B cell clone. Thus, the effect of estrogens and HCG on lymphopoiesis may be indirect, as, for example, on stromal cells, or may be on a very early stage in the B cell lineage. Studies with progesterone and sorted B cell precursors indicate that lymphocyte precursors are directly affected by this hormone, as described in Example 3.

In a preferred embodiment for in vitro modulation, a quantity of the hormone in a concentration effective in inducing the desired modulation in the production of B lymphocyte precursor cells by proliferation or differentiation, as determined by the routine assays described above and in the examples, is added to a culture medium suitable for growing lymphoid cells in or upon which bone marrow samples or sorted B precursor cells are placed. A preferred starting amount of hormone is in the range between $10^{-10}$ and $10^{-4}$ M hormone in medium, which can be adjusted to achieve the desired results.

Based on these discoveries, one would also select culture media for cells that differentiate or proliferate to form new B lymphocytes which does not contain hormones that are elevated during pregnancy, or compounds determined to mimic the activity of these compounds, such as some of the dyes common in culture media as pH indicators.

It has long been an objective to establish and optimize conditions for maintenance of lymphopoietic, myelopoietic, and erythropoietic progenitors and stem cells in culture. Some success has been achieved in this regard with murine bone marrow cells, but success is generally more limited with human cells. The ability to maintain and expand human stem cells in culture would provide a new approach to bone marrow transplantation and facilitate introduction of new genes.

Insufficient attention has been paid to the role of hormones in hemopoiesis. For example, it is believed that titration of various hormones in culture media can result in improved survival and/or differentiation of particular cell types.

It has been demonstrated that hormones can both stimulate and inhibit production of selective groups of precursor and mature lymphocytes by proliferation or differentiation, both in vitro and in vivo. Therefore, it is believed that culture of these cells can be improved not only by administration of the hormones or agents that stimulate precursor cell proliferation, but also by omission or deletion of compounds that suppress proliferation through estrogenic or progesterogenic effects, such as phenol red, a dye commonly used as a pH indicator that has estrogenic activity, or animal sera containing inappropriate hormones or non-physiologic concentrations of hormones. Accordingly, culture medium formulations that are either serum free or contain low concentrations of estrogen (fetal calf serum depleted by charcoal extraction or freon treatment) and no phenol red should be used.

Culture medium formulations may also be made to contain a variety of pregnancy related and other hormones, which can be titrated into cultures of mammalian bone marrow with this medium to determine which compounds stimulate or depress B cell precursor production by proliferation or differentiation. Hormones to be tested in this way include estrogens, progesterone, human chorionic gonadotropin (HCG), human placental lactogen, growth hormone, follicle stimulating hormone (FSH), luteinizing hormone (LH), dihydrotestosterone, vitamin D3, prolactin, glucocorticoids, and releasing factors such as GNRHs. Doses will range from $10^{-10}$ to $10^{-4}$ M final concentrations.

The present invention will be further understood by reference to the following non-limiting examples.

Example 1

Selective suppression of B lineage precursors in pregnant animals.

The incidence of B lymphocyte precursors in bone marrow dramatically declines during pregnancy and, depending on whether lactation is permitted, regenerates after delivery. Precursors of other types of blood cells are present in either normal or slightly elevated numbers during pregnancy.

B lymphocyte lineage precursors that are responsive to interleukin 7 (IL-7) from pregnant mice were assayed with a semisolid agar cloning technique, as reported by Lee et al., J. Immunol. 142:3875 (1989). FIG. 1 is a graph showing the number of IL-7 responsive B lineage precursors versus days of gestation and days postpartum for normal mice, expressed as the percent of control. Bone marrow cells were obtained from BALB/c mice at various stages of pregnancy and during the postpartum period and placed in semisolid agar with IL-7. The numbers of proliferating foci were determined after six days of culture.

The results show a significant depression in numbers of B lineage precursor cells but not mature B cells. Numbers of responding cells in maternal bone marrow were very reduced within six days of gestation and averaged about 10% of normal throughout pregnancy. The numbers returned to normal after delivery, and did so most dramatically when offspring were removed from the mother at the time of birth.

Figure 2A:
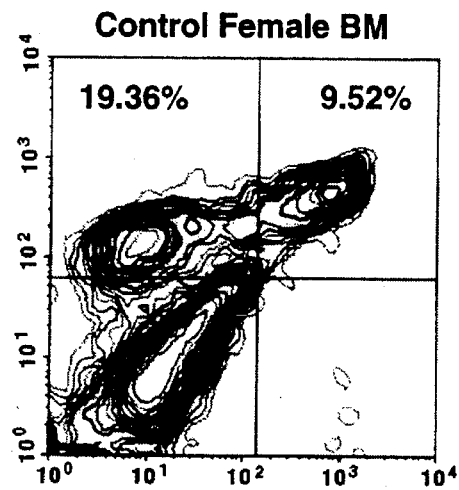
FIGS. 2A, 2B, 2C, and 2D show by flow cytometry the analysis of B lineage precursors in bone marrow of control and pregnant mice. In each figure, cells in the upper right quadrant represent B lymphocytes, and cells in the upper left quadrant are B lineage precursor cells.
Figure 2B:
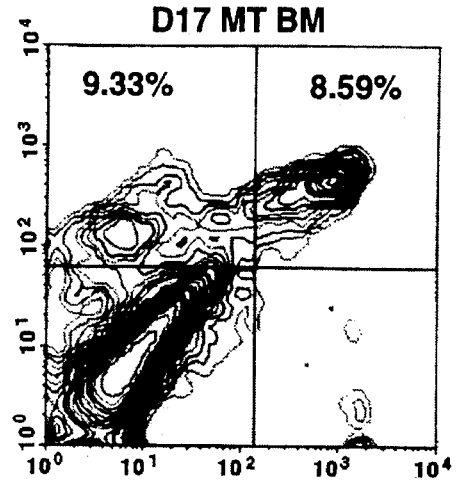
Figure 2C:
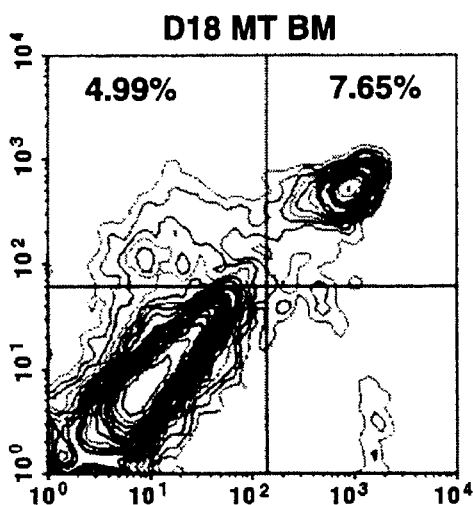
Figure 2D:
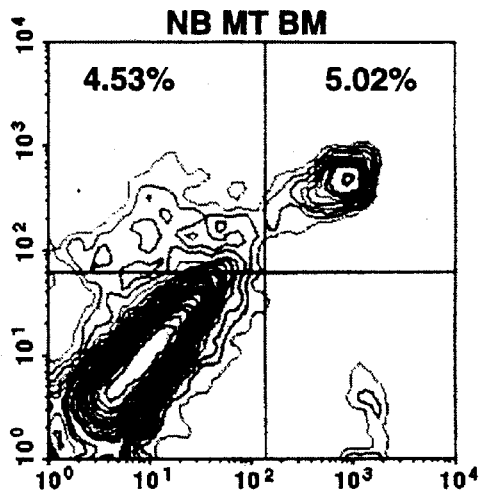

FIGS. 2A, 2B, 2C, and 2D show by flow cytometry the analysis of B lineage precursors in bone marrow of control and pregnant mice. FIG. 2A shows the results in normal control mice. FIG. 2B illustrates the analysis at 17 days gestation. FIG. 2C shows the results at 18 days gestation. FIG. 2D represents the results at term. Single cell suspensions of bone marrow were prepared and stained with an FITC labeled antibody to IgM (Southern Biotechnology Assoc., Birmingham, Ala.). The same preparations were treated with a biotin labeled monoclonal antibody (14.8) to murine CD45RA. This reagent was then detected with an additional step, in which the cells were stained with phycoerythrin (PE) labeled streptavidin. Simultaneous two color analysis was then performed on individual cells with a BD FACScan flow cytometer. Cells in the upper right quadrants represent B lymphocytes. Their numbers did not change significantly during pregnancy. In contrast, B cell precursor numbers markedly declined, as shown in the upper left quadrant at 17 and 18 days gestation and at term.

Figure 3:
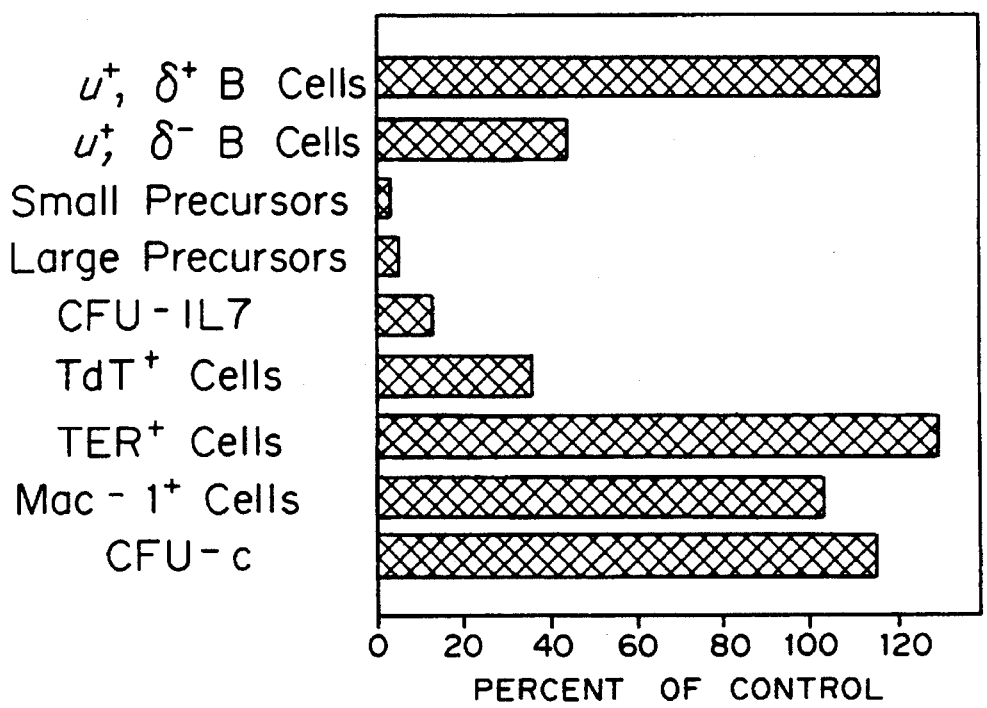
FIG. 3 is a bar graph showing the effects of pregnancy on bone marrow cells, expressed as a percent of control. Cell types are $\mu^+$, delta$^+$ B cells; $\mu^+$, delta$^-$ B cells, small precursors; large precursors; CFU-IL7 cells; TdT$^+$ cells; TER$^+$ cells; Mac-1 cells; and CFU-c.

Other assays were then used to enumerate cells with B lymphocyte precursor characteristics. FIG. 3 is a bar graph of the effects of pregnancy on numbers of bone marrow cells as a percent of control. Cell types are $\mu^+$, delta$^+$ B cells; $\mu^+$, delta$^-$ B cells; small precursors; large precursors; CFU-IL7 responsive cells; TdT$^+$ cells; TER$^+$ cells; Mac-1$^+$ cells; and CFU-c. The only significant declines found were in cells identified as precursors of B lineage lymphocytes. Early cells in this series contain the enzyme terminal deoxynucleotidyl transferase (TdT), and they give rise to large precursors, which are also detectable with the IL-7 cloning assay. Small pre-B cells represent the immediate precursors of immature new B cells. Mature B lymphocytes are discriminated on the basis of IgD expression.

The number of cells containing the enzyme TdT was depressed in pregnant animals, as was the number of cells expressing surface markers typical of IL-7 responsive cells, large and small pre-B cells, and, to a lesser extent, immature B lymphocytes. These markers include CD45RA, CD43, heat stable antigen (HSA), the absence of surface immunoglobulin D, and the presence of mu chains of immunoglobulin. Numbers of mature B cells, as determined by immunofluorescence and flow cytometry to bear surface IgM and IgD, in bone marrow and other tissues were not depressed. Moreover, bone marrow cells with characteristics of erythroid and myeloid cells were present in normal or slightly elevated numbers. These cells were assessed with a cloning assay for granulocyte-macrophage progenitor cells (CFU-c assay) and immunofluorescence with TER 119 (provided from Dr. T. Kina, Kyoto, Japan) and Mac-1 monoclonal antibodies (obtained from the American Type Culture Collection, Rockville, Md.).

These results are in accordance with observations that the immune system functions normally during pregnancy in defense against pathogens. Most of the mature B lymphocytes are probably memory cells that have been involved in or developed from previous immune responses and that may survive for years. It is possible that the precursor cells are suppressed during pregnancy to avoid rejection of the fetus. However, a long term suppression of new B lymphocyte production may lead to a diminished and faulty regulation of the immune system. This could be a factor in the higher frequency of diagnosis of autoimmune disorders in pregnant women.

Example 2

Hormone induced suppression of B lineage precursor cells.

To determine whether hormones that normally increase in endogenous levels during pregnancy are responsible for the decreased numbers of B lymphocyte precursor cells in bone marrow during pregnancy, normal non-pregnant female mice were implanted with pellets containing hormone and studied at intervals thereafter. Normal BALB/c female mice were used for all studies and were at least 8 weeks old. Pellets containing placebo or graded concentrations of hormones were obtained from Innovative Research of America, Toledo, Ohio. Three estrogens: estrone, estradiol, and estriol, alone or in combination with progesterone, were tested.

Figure 4A:
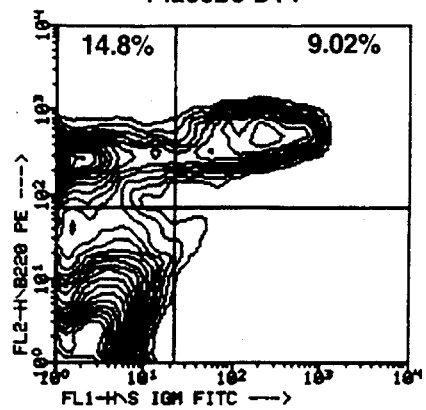
FIGS. 4A, 4B, 4C, 4D, and 4E illustrate the analysis by flow cytometry of the dose dependent depression in numbers of B lineage precursors after the implantation of pellets containing estrogen into normal mice. Normal BALB/c female mice were given pellets containing placebo (FIG. 4A) or 2.5 mg of 17 β-estradiol (FIG. 4B), estriol (FIG. 4C), estrone (FIG. 4D), or DHEA (FIG. 4E). Bone marrow samples were collected after two weeks of treatment and analyzed as described with reference to FIGS. 2A–D.
Figure 4B:
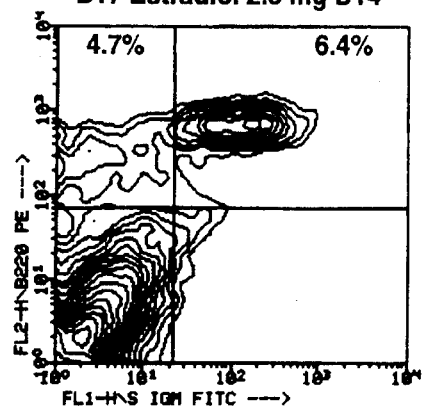
Figure 4C:
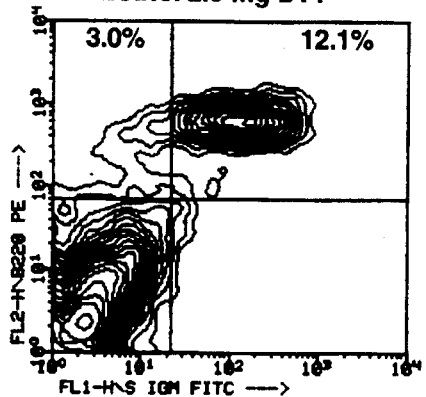
Figure 4D:
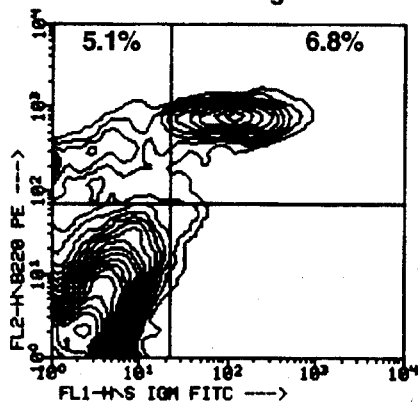
Figure 4E:
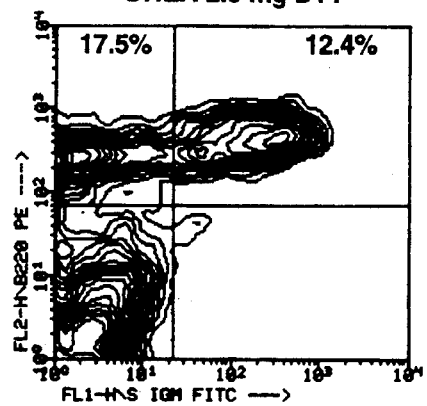

FIGS. 4A, 4B, 4C, 4D, and 4E show results of the analysis by flow cytometry of the dose dependent depression of B lineage precursors after the implantation of estrogen-containing pellets into normal mice. Normal BALB/c female mice were given pellets containing placebo (FIG. 4A) or 2.5 mg of 17 β-estradiol (FIG. 4B), estriol (FIG. 4C), estrone (FIG. 4D), or DHEA (FIG. 4E). Bone marrow samples were collected after two weeks of treatment and analyzed as described, with reference to FIGS. 2A–2D.

Results are shown numerically in Table I.

TABLE I

Selective Depletion of B Cell Precursors by Estrogen Treatment.

| Assay | placebo | estradiol | estriol | estrone | DHEA |
|---|---|---|---|---|---|
| pre-B | 33 ± 5 | 3 ± 1 | 0 | 3 ± 3 | 20 ± 3 |
| myeloid | 70 ± 15 | 103 ± 12 | 126 ± 42 | 101 ± 23 | 143 ± 17 |
| B cells | 44 ± 11 | 75 ± 20 | 174 ± 40 | 45 ± 14 | 74 ± 5 |

Estrogen pellets containing 2.5 mg of hormone were effective at simulating the effects of pregnancy on B lymphocyte precursor cells and caused a selective depletion of B lymphocyte precursors in bone marrow. Changes in subpopulations of B lymphocyte lineage cells were similar to those in pregnant mice, as described in Example 1.

Progesterone pellets, when used alone, had no effect. However, progesterone greatly enhanced the suppression mediated by estrogen when the two hormones are used together. Mice exposed to progesterone were sensitive to concentrations of estrogen lower by at least one order of magnitude than the concentrations of estrogen used alone.

Experiments were done to determine whether short term hormone treatment affected the numbers of B lymphocyte lineage precursors. Male and female mice received acute treatment with single injections of water soluble estradiol. Mice of both sexes were sensitive to estrogens in this protocol. Total numbers of nucleated cells and myeloid progenitor cells in bone marrow remained unchanged. IL-7 responsive B lymphocyte precursors dramatically declined within one day of injection. There was a subsequent sharp drop in small pre-B cells four days after this transient elevation in estrogen.

These experiments demonstrate that B lymphopoiesis is sensitive to negative regulation by sex steroids.

Example 3

Effects of hormone addition in cell culture.

Experiments were done to determine whether hormones modulate the production of B lymphocytes in culture.

Two systems were used for examining the effects in long term bone marrow culture models, which contain both parenchymal and stromal cells. The first, which supports growth of B lymphocyte lineage cells, was sensitive to addition of estradiol. In contrast, a second type of culture, which maintains growth of non-lymphoid (myeloid) cells in vitro, was unaffected by the same hormone.

Long term bone marrow cultures were then set up under Whitlock-Witte (lymphoid) or Dexter culture conditions, as described in detail by Witte et al., *Eur. J. Immunol.* 17:1473 (1987), and Hayashi et al., *Blood* 74:1711 (1989), and hormones were added to certain groups of culture flasks.

Estrogen suppressed lymphocyte production in long term culture but had no effect on proliferation of myeloid cells that had reached this stage of maturation. Some hormones, such as progesterone, had no effect on either type of culture.

Figure 5:
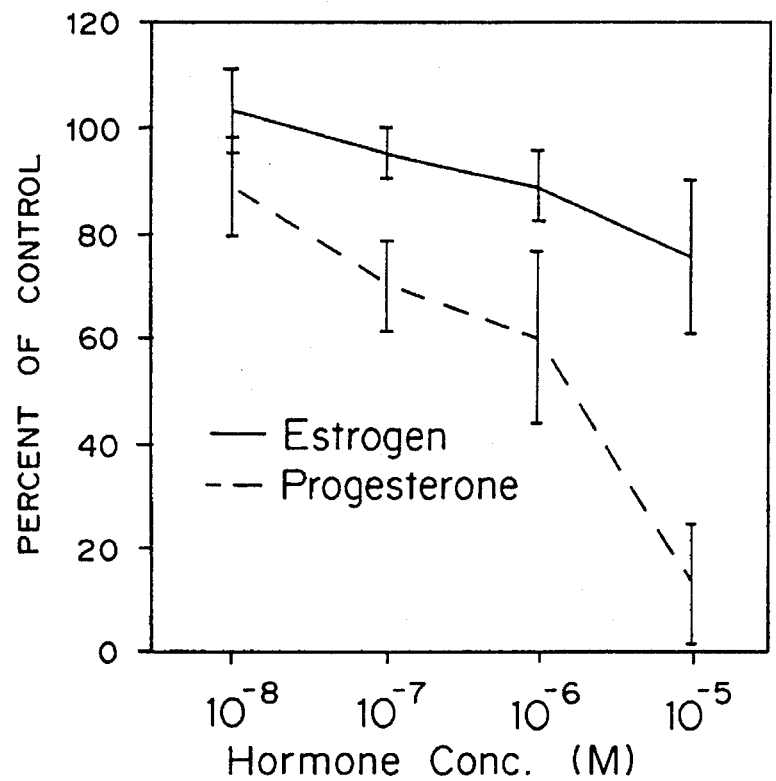
FIG. 5 is a graph illustrating the effects of estrogen and progesterone on sorted B cell precursors plated in semisolid agar cultures with IL-7, expressed as percent of control of the number of pre-B cell colonies occurring after six days of culture for hormone concentrations between $10^{-8}$ and $10^{-5}$ M.

Experiments were also performed to assess the effects of sex steroid hormones on B lymphocyte and precursor cell production in cultures lacking stromal cells. Sorted B cell precursors were plated in semisolid agar cultures with Il-7, which stimulates pre-B cell production. Estrogen or progesterone were added to the cultures at concentrations of $10^{-8}$, $10^{-7}$, $10^{-6}$, and $10^{-5}$ M, and the numbers of pre-B cell colonies were counted after six days of culture. The results are shown in FIG. 5. Progesterone inhibited the proliferation of B cell precursors, while estrogen had minimal activity.

These results indicate that bone marrow is a direct target of hormone action and that production of a discrete population of blood cells is selectively influenced.

Further experiments were performed to determine the effects of sex steroid hormones on B lymphocyte precursor production in co-cultures of stromal cells and lymphocyte precursor cells. B lymphocyte precursors (fractions A and B) were sorted on the basis of their expression of CD45R, CD43, and low levels of heat stable antigen (HSA). These cells were placed in culture on top of cloned stromal cells (42OP) with added IL-7. Estrogen (E2) and insulin like growth factor (IGF-I) were added to the cultures. Numbers of cells recovered four days later were normalized to the number initially placed in culture.

Figure 6:
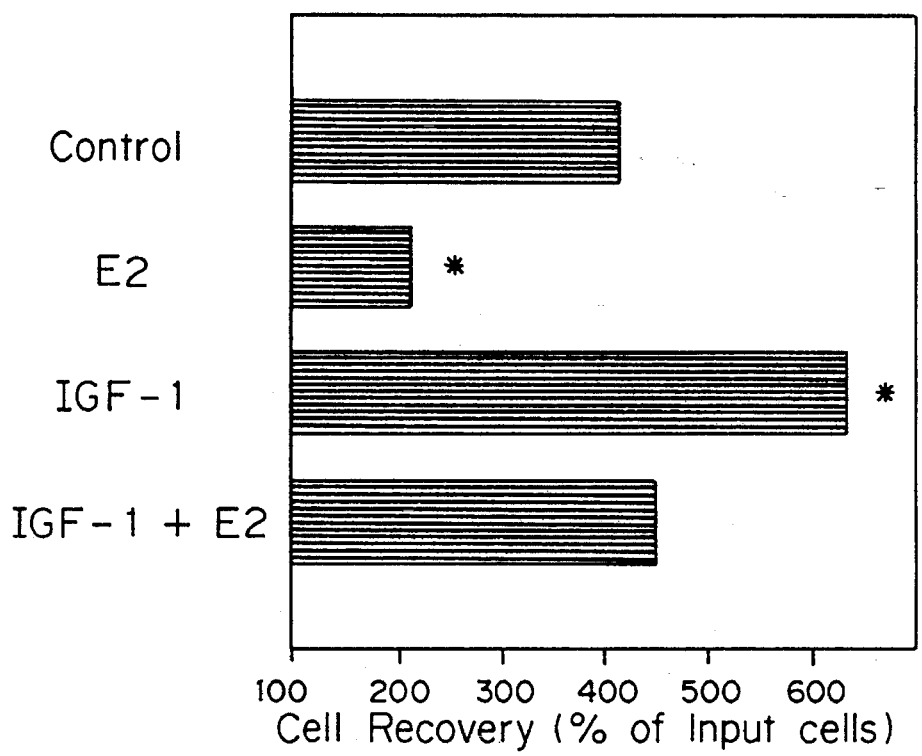
FIG. 6 is a bar graph showing the effects of estrogen (E2) and insulin like growth factor (IGF-I), alone and in combination, on B lineage precursors (Fractions A and B) grown in culture on top of bone marrow stromal cells with added IL-7. Cells were recovered after four days and values were normalized to the number of cells placed in culture initially and expressed as cell recovery (per cent of input cells).

The results are shown in FIG. 6. In contrast to the model in which estrogens had only limited effect on the number of B precursor cells cultured without stromal cells, estrogens depress the survival and/or proliferation of B precursor cells in the co-culture model, indicating that this assay may contain an earlier lymphocyte precursor that is estrogen sensitive and/or that stromal cell functions are subject to regulation by this hormone and mediate the effects of estrogen. Insulin like growth factor (IGF-I) enhances the production of B precursor cells but does not completely overcome their sensitivity to estrogen.

Example 4

Effect of hormones on calcium deposition by stromal cells.

An interesting and potentially important effect was noted in the long term bone marrow culture model with another hormone. Human chorionic gonadotropin (HCG) caused more rapid than normal proliferation of cells in the adherent layer. The adherent layer is made up of bone marrow stromal cells that include, among other cells, adipose cells, macrophages, multipotential adventitial cells, reticular cells, fibroblast-like cells, and undifferentiated mesenchymal cells.

One interesting result that has been obtained with HCG is that it appears to cause the deposition of calcium by stromal cells in the adherent layer in a long term bone marrow culture. This hormone may induce certain of the stromal cells to differentiate into osteoblasts or osteoblast-like cells, a finding that could have implications for attempts to accelerate or control bone formation. Certain stromal or parenchymal cells of bone marrow may respond to estrogens indirectly, as a result of interaction of the estrogen with other bone marrow cells and/or regulatory cytokines. For example, estrogen might induce production of interleukin I or TGF-β, both of which are known inhibitors of B lymphocyte production. This induction could be indirect, as for example if estrogen induced cathepsin D, which in turn activated TGF-β via proteolytic action on a latent form. There is also reason to suspect that hormones may regulate the expression and/or function of cell adhesion molecules, such that retention of immature cells in marrow is affected.

Agents that interfere with the synthesis or activity of estrogens, HCG, gonadotropins, GNRH, and other hormones that are elevated during pregnancy could also influence the deposition of calcium by stromal or other cells in the adherent layer and could have implications in the regulation of bone formation.

Example 5

Selective increases in production of B lineage precursors in hypogonadal mice.

The absence of function of the hormones elevated during pregnancy, due to genetic deficiencies; the absence or malfunction of the hormone-producing cells; or the administration of agents that interfere with the synthesis or activity of these hormones or their eliciting agents and regulators, such as agonists, antagonists, competitive inhibitors, inactivators, blockers, or other compounds, resulting in lowered endogenous levels of the pregnancy-related hormones, can positively modulate B lymphopoiesis. Positive modulation results in increased production of B lymphocyte precursor cells, as indicated by the following studies using genetically hypogonadal mice and castrated mice.

Hypogonadal HPG/Bm-hpg/hpg mice have a partial deletion of the hypothalamic gonadotropin releasing hormone (GNRH) gene, resulting in infantile reproductive tracts and a failure to synthesize gonadotropins, such as luteinizing hormone and follicle stimulating hormone, and sex steroid hormones. It was found that these mice have a greatly expanded population of IL-7 responsive B lineage precursors, and that estrogen replacement resulted in a dose dependent reduction in B cell precursors. More modest increases were documented in mice that were surgically castrated.

In experiments directed at determining the effects of the absence of gonadotropin releasing hormones (GNRH) on B lymphocyte lineage cells, the hypogonadal mutation was maintained within the HPG/Bm inbred strain of mice, and phenotypic heterozygous littermate animals were used as controls. Mutant hpg/hpg mice were identified by Southern blot analysis, as described by Beamer et al., 53 *Cancer Res.* 3741 (1993), and confirmed by measurement of uterine weights. Doubly deficient hypogonadal scid/scid mice were produced as described by Beamer et al. Castrated mice were obtained from Charles Rivers (Wilmington, Mass.).

For colony assays used to determine the numbers of B lymphocyte precursor cells, bone marrow cells were prepared and suspended in 1 ml assay medium as described by Lee et al., 142 *J. Immunol.* 3875 (1989). The semisolid agar cloning assay for B lymphocyte precursor cells (CFU IL-7) was done with 10 ng recombinant mouse IL-7 (Immunex, Seattle, Wash.). Mitogen responsive B cells were detected with 25 µg/ml of endotoxin (Difco, Detroit, Mich.), and the granulocyte/macrophage progenitor assay (CFU-G/M) was done with 25 µl of 10 times concentrated L cell conditioned medium. All cloning assays were performed in 35mm dishes (Corning Glass, Inc., Corning, N.Y.) and incubated at 37° C., 5% $CO_2$. Colonies were scored on day six.

Immunofluorescent staining and analysis techniques were used to assess numbers of cells in subpopulations of B lymphocyte lineage cells. Cells were suspended in staining buffer (PBS without $Ca^{++}$ and $Mg^{++}$ with 3% heat inactivated FCS and 0.1% sodium azide) at a concentration of 107 cells per ml. Staining was performed by incubating cells with antibodies on ice for 15 minutes and then washing with 10 volumes of staining buffer. Unconjugated antibodies were revealed by a subsequent incubation with the appropriate fluorochrome-conjugated second antibody, or in the case of biotinylated primary antibodies, with streptavidin phycoerythrin (PE) (Biomeda, Foster City, Calif.) or streptavidin Peridinin CP (Becton Dickinson, Mountain View, Calif.). B cells were identified by staining with FITC labeled goat anti-IgM (Southern Biotechnology, Birmingham, Ala.).

Subpopulations of B lineage precursors were then resolved using a second aliquot of the same cell suspensions with a modification of the procedures described by Hardy et al., 173 *J. Exp. Med.* 1213 (1991). As a first step, B cells were depleted by adherence on anti-IgM coated plastic dishes. The remaining cells were then stained with FITC labeled MI/69 (HSA, heat stable antigen) (Pharmingen, San Diego, Calif.); or as culture supernatant from hybridoma TIB125 (American Type Culture Collection, ATCC, Rockville, Md.), biotinylated-S7 (CD43) purified and biotinylated from the hybridoma obtained from the ATCC; and PE labeled 6B2 (CD45R) (Pharmingen).

This three color analysis was then performed and interpreted according to the following characterizations: Very early B lymphocyte precursors (referred to by Hardy et al. as Fraction A) are discriminated by their low expression of HSA and are $CD43^+$. More mature pro-B and large pre-B cells (Fractions B+C) are also $CD43^+$ but display high levels of HSA. Small pre-B lymphocyte precursors are $CD45R^+$ and $CD43^-$ (Fraction D). All samples were analyzed with a FACScan flow cytometer (Becton Dickinson). Parameters were established for discriminating total nucleated cells and lymphocytes by staining with appropriate antibodies, backgating on the positive cells, and setting forward and orthogonal scatter gates. These methods of analysis are known and routinely performed by those skilled in the art.

The significance of differences was evaluated statistically by paired t testing.

Figure 7:
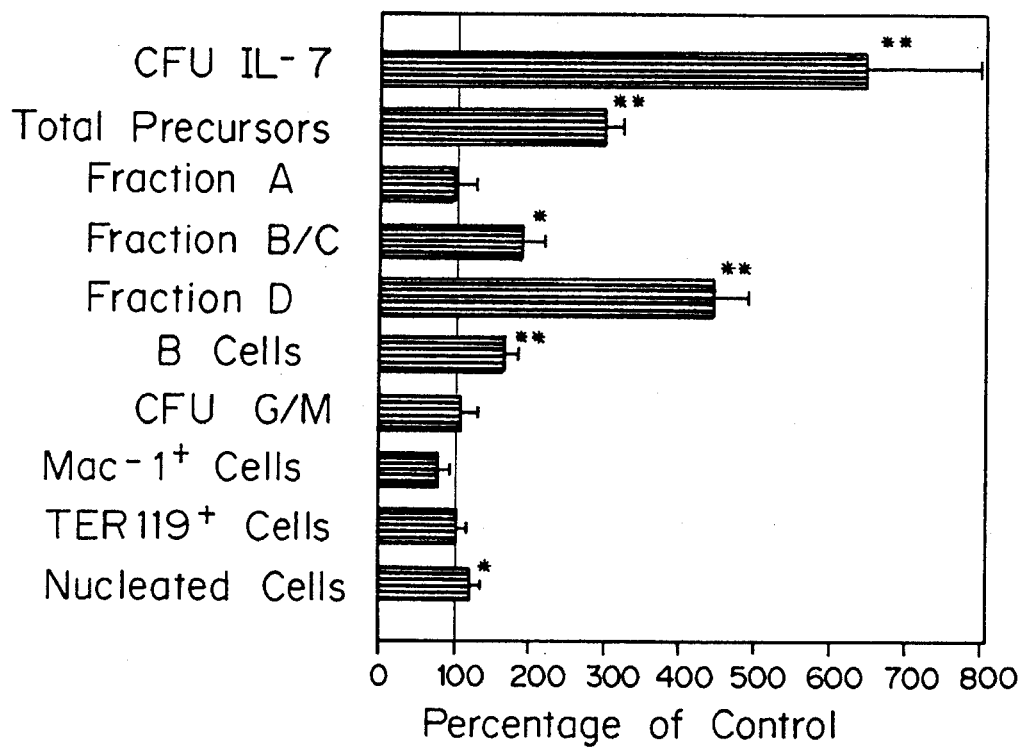
FIG. 7 is a graph comparing the numbers of lymphoid and myeloid cells in bone marrow of littermate normal and genetically hypogonadal (hpg/hpg) mice, based on colony assays enumerating IL-7 responding cells (CFU IL-7) and myeloid progenitor cells (CFU-G/M) and on flow cytometry assessments of total B lineage precursors, fraction A cells, fraction B/C cells, fraction D cells, and mature B cells. Results were normalized to the normal littermate controls, and statistical significance is indicated by asterisks (*, p=<0.05; **, p=<0.01).

In the hypogonadal mice, IL-7 responding B lymphocyte precursors (CFU IL-7) were readily identified with the clonal assays, as described by Lee et al., Id. Numbers of these precursors were dramatically elevated in bone marrow of homozygous mutant hpg/hpg mice, as shown in FIG. 7. Highly significant increases were also detected in total B lymphocyte lineage precursors ($CD45R^+$, $sIgM^-$) enumerated by flow cytometry. Multiparameter flow cytometry was then used to resolve subpopulations of these cells at various stages of differentiation, using the characterization method of Hardy et al., 173 *J. Exp. Med.* 1213 (1991).

The frequency of cells at a very early stage ($CD45R^+$, $HSA^{lo}$, $CD45^+$, Fraction A) was normal in hpg/hpg mice. Subsequent compartments ($CD45R^+$, $HSA^{hi}$, $CD43^+$, Fractions B/C), including the clonable IL-7 responding cells, were significantly elevated in hpg/hpg mice. However, small pre-B cells ($CD45R^+$, $HSA^{hi}$, $CD43^-$, Fraction D) represented the most substantially increased subpopulation. This is reciprocal to the situation in pregnant or estrogen treated mice, where small pre-B cells were the most depressed of all B lineage cells, as shown in examples 1 and 2.

The significant elevations in B cells in bone marrow of hpg/hpg mice (1.7 fold increase, p=0.003, FIG. 7) included not only cells with immature characteristics ($sIgM^+$, $sIgD^-$ and $sIgM^+$, $HSA^{hi}$), but also mature B lymphocytes ($sIgM^+$, $sIgD^+$).

B cells in the spleen, including immature and mature populations, were significantly increased by approximately two fold. Nucleated cells as a whole were increased by the same amount, but there was no significant change in $Mac-1^+$ cells in that site. Thus, changes in B lineage precursors within bone marrow were accompanied by some expansion of peripheral B lymphocytes.

As in the pregnancy studies, the elevations in numbers of B lymphocyte precursor cells in bone marrow of hpg/hpg mice were highly selective, as shown in FIG. 7. Numbers of total nucleated cells were modestly but significantly increased in hpg/hpg bone marrow, a change accounted for by increases in B lineage lymphocytes. Numbers of myeloid progenitors detected with a clonal assay (CFU-G/M) and myeloid and erythroid cells enumerated by flow cytometry (with Mac-1 and TER 119 antibodies) were all within the normal range.

The hpg mutation did not overcome the B cell deficiency in doubly mutant hypogonadal, severe combined immunodeficiency (hpg/hpg scid/scid) mice. There were significant elevations in B lineage precursors (p=<0.001) but less pronounced elevations in mature B cell numbers.

Example 6

Selective decrease of B lineage precursor numbers in hypogonadal mice treated with estrogen.

Figure 8:
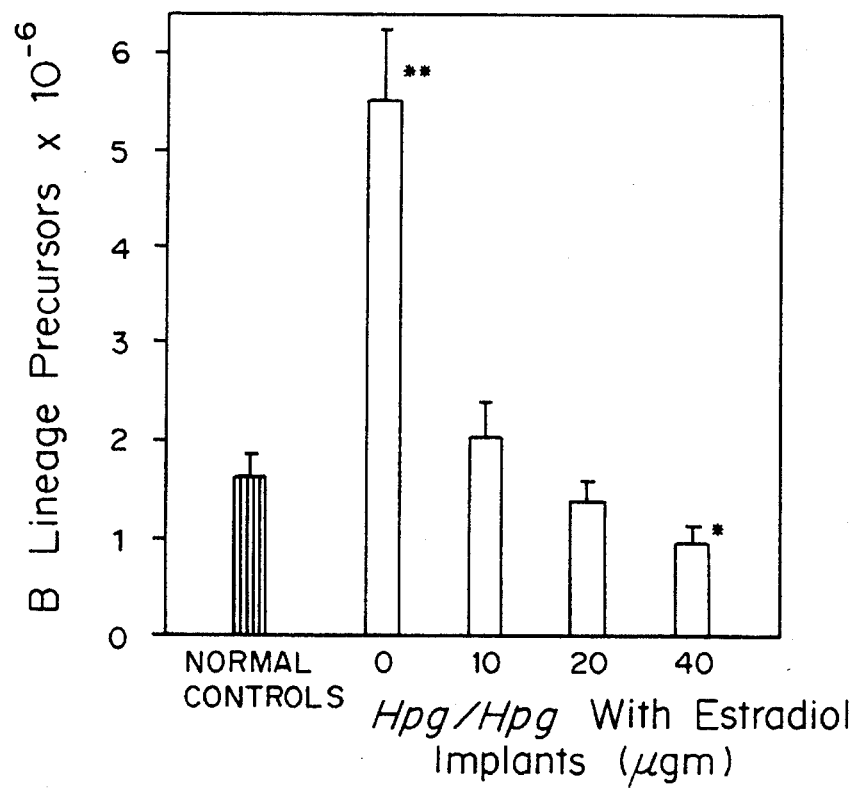
FIG. 8 is a graph showing B lineage lymphocyte precursor numbers in bone marrow of normal control and hpg/hpg mice based on two color flow cytometry assessments performed at five weeks after implantation of 17 β-estradiol (0, 10, 20, and 40 μg) or control tubing. Highly significant (**, p=<0.001) and significant (*, p=0.036) differences from control values are indicated.

The hypogonadal mutation ablates synthesis of the GNRHs, which in turn abolishes synthesis of gonadotropins (follicle stimulating and luteinizing hormones). Any of these hormones or the sex hormones regulated by the gonadotropins could be responsible for the observed increase in numbers of B lymphocyte precursor cells. To determine whether sex hormone replacement affected B lineage cell populations in hypogonadal mice, five to six week old female hpg/hpg mice were implanted with elastomer medical grade tubing (Silastic™, Dow Corning Corp. Medical Products, Midland, Mich.) containing 10, 20, or 40 μg 17 β-estradiol and 8 mg cholesterol or control tubing containing cholesterol alone. Assays of B lineage cells were performed as described in examples 1 and 5. As illustrated in FIG. 8, the sustained elevations in serum estrogen resulted in a dose dependent decrease in B lineage cells. These results indicate that the deficiency in sex steroids allows the expanded lymphocyte production in the mutant mice.

This implant procedure is known to cause an osteosclerotic reaction in the peripheral bones of normal mice, and fewer nucleated cells were recovered from estrogen treated hypogonadal mice. However, it was clear from subset analysis that this sex hormone preferentially depressed B lineage precursors and that the highest dose brought their numbers below the normal range. Thus, B lymphopoiesis in the mutant animals is sensitive to preferential negative regulation by this estrogen, demonstrating again that systemic levels of sex steroids correspond reciprocally to the production of new cells within bone marrow.

Example 7

Selective increases in production of B lineage precursors in castrated mice.

Numbers of B lymphocyte lineage precursor cells were also evaluated in castrated mice. Castrated mice lack the major sources of endogenous sex steroid hormones, namely testes and ovaries, but may have some production of sex steroid hormones or precursor molecules in cells of other organs such as the adrenal gland.

BALB/c mice (nine of each sex), 3 weeks of age, were surgically castrated under anesthesia by methods known to those skilled in the art. Control mice were sham operated under the same conditions. Using the methodology described in examples 1 and 5, bone marrow cells were obtained from the mice two to three weeks after castration and placed in semisolid agar with IL-7. The numbers of proliferating foci were determined after six days of culture. Subpopulations of B lineage precursors in the bone marrow were assayed by the flow cytometry techniques and assays for surface markers, also described in examples 1 and 5.

In male mice, the numbers of IL-7 responsive cells and small pre-B cells in bone marrow increased approximately two fold after castration, as compared to sham operated controls (p<0.001 for both). These numbers were variable in ovariectomized BALB/c mice, and no significant changes were found (p=0.863 and p=0.310, respectively). However, significant elevations (1.6 fold) in B lineage cells were found when females of the same strain as the hypogonadal mice (HPG/Bm−+/−) were ovariectomized (p=0.022).

These experiments demonstrate that manipulations that decrease the levels or the functional activity of GNRHs, gonadotropins, sex steroid hormones, or other hormones that are elevated during pregnancy, including genetic alterations in the cells that synthesize and secrete these compounds, removal of the hormone-producing cells, or the administration of agents that interfere with the synthesis or activity of any of these hormones, can positively modulate B lymphopoiesis, resulting in increased production of B lymphocyte precursor cells.

Modifications and variations of the present invention will be obvious to those skilled in the art from the foregoing detailed description. Such modifications and variations are intended to come within the scope of the following claims.

We claim:

1. A method for modulating production of committed mammalian B lymphocyte precursor cells in an animal that has normal bone marrow comprising exposing the cells to a hormone selected from the group consisting of hormones elevated during pregnancy, synthetic analogues of the hormones elevated during pregnancy, eliciting agents of the hormones elevated during pregnancy, and agents that interfere with the synthesis or activity of the hormones elevated during pregnancy, in an amount effective to alter selectively production of B lymphocyte precursor cells by proliferation or differentiation as compared with proliferation of mature B lymphocytes.

2. The method of claim 1, wherein the hormone is selected from the group of natural and synthetic hormones consisting of estrogen, estrone, estradiol, estriol, progesterone, and combinations thereof, and the amount is effective to inhibit production of B lymphocyte precursor cells by proliferation or differentiation.

3. The method of claim 1, wherein the agent that interferes with the synthesis or activity of the hormones elevated during pregnancy is selected from the group consisting of agonists, antagonists, competitive inhibitors, inactivators, and blockers, alone or in combination, of the hormones elevated during pregnancy.

4. The method of claim 1, wherein the hormone is administered to cells in culture.

5. The method of claims 4, wherein the cells are bone marrow cells in culture.

6. The method of claim 1, wherein the hormone is an agent that interferes with the synthesis and activity of the hormones elevated during pregnancy and the amount is effective to increase production of B lymphocyte precursor cells by proliferation or differentiation.

7. The method of claim 6, wherein the agent is selected from the group consisting of RU 486, ICI 182,780, aromatase inhibitors, and gonadotropin releasing hormone agonists.

8. The method of claim 7, wherein the aromatase inhibitors are selected from the group consisting of 1,4,6-androstatriene-3,17-dione and 4-hydroxyandrostenedione.

9. The method of claim 1, wherein the hormone is selected from the group consisting of chorionic gonadotropin, hormone eliciting agents, agents that interfere with the synthesis or activity of the hormones elevated during pregnancy, and combinations thereof and the amount is effective to manipulate production of B lymphocyte precursor cells by proliferation or differentiation in animals and man.

10. The method of claim 9, wherein the hormone is administered to a patient in need of treatment to modulate production of committed mammalian B lymphocyte precursor cells.

11. The method of claims 10, wherein the patient has an autoimmune disorder and the amount is effective to decrease production of B lymphocyte precursor cells by proliferation or differentiation and thereby decrease production of mature B lymphocytes that secrete autoantibodies.

12. The method of claim 10, wherein the patient has a humoral immune deficiency disease and the amount is effective to increase production of B lymphocyte precursor cells by proliferation or differentiation and thereby increase production of mature B lymphocytes in an amount effective to alleviate the symptoms of the immune deficiency disease.

13. The method of claims 10, further comprising administering to a patient in need of treatment to modulate production of committed mammalian B lymphocyte precursor cells a hormone selected from the group consisting of chorionic gonadotropin, hormone eliciting agents, agents that interfere with the synthesis or activity of the hormones elevated during pregnancy, and combinations thereof in an amount effective to increase calcium deposition by stromal cells of bone marrow.

* * * * *